United States Patent [19]

Nishioka et al.

[11] Patent Number: 4,720,178
[45] Date of Patent: Jan. 19, 1988

[54] OPTICAL SYSTEM FOR ENDOSCOPE

[75] Inventors: Kimihiko Nishioka; Tsutomu Yamamoto; Susumu Takahashi; Akira Yokota, all of Hachioji, Japan

[73] Assignee: Olympus Optical Co., Ltd., Japan

[21] Appl. No.: 765,355

[22] Filed: Aug. 13, 1985

[30] Foreign Application Priority Data

Aug. 15, 1984 [JP] Japan ............................ 59-169380

[51] Int. Cl.⁴ .................. A61B 1/04; G02B 5/04; G02B 5/22; G02B 5/30
[52] U.S. Cl. ........................ 350/401; 128/4; 128/5; 350/1.1; 350/286
[58] Field of Search .............. 128/4, 6, 5, 7, 8; 350/400, 401, 618, 286, 1.1

[56] References Cited

U.S. PATENT DOCUMENTS

| | | | |
|---|---|---|---|
| 1,698,124 | 1/1929 | De Zeng | 350/1.1 X |
| 3,095,475 | 6/1963 | Brake | 350/162.17 X |
| 3,901,220 | 8/1975 | Koyasu et al. | 350/168 X |
| 4,113,354 | 9/1978 | Yamasita | 128/4 X |
| 4,310,228 | 1/1982 | Terada | 128/6 X |
| 4,626,897 | 12/1986 | Sato et al. | 350/401 X |

FOREIGN PATENT DOCUMENTS 58-46922 3/1983 Japan .

Primary Examiner—John K. Corbin
Assistant Examiner—D. Edmondson
Attorney, Agent, or Firm—Ostrolenk, Faber, Gerb & Soffen

[57] ABSTRACT

An optical system is disclosed for an endoscope having a generally tubular distal end in which an objective lens assembly and a solid-state video camera are internally housed so that an image formed by the lens assembly is focussed upon the video camera. The video camera is disposed along or in proximity to the center axis of the distal end of the endoscope. The video camera may be positioned in this way due to the provision of a reflecting surface which is angularly disposed in opposing relationship with an input surface of the video camera, and deflection means disposed in front of the lens assembly and within the objective lens assembly, or between the lens assembly and the reflecting surface, so that an image formed by the lens assembly can be focussed on the input surface of the video camera.

12 Claims, 22 Drawing Figures

F I G. 18
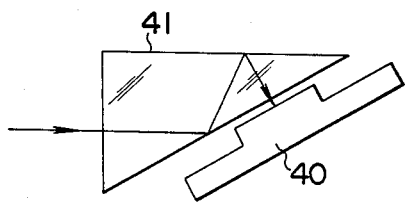
F I G. 19
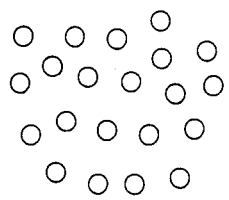

OPTICAL SYSTEM FOR ENDOSCOPE

BACKGROUND OF THE INVENTION

1. Field of the Invention

The invention relates to an optical system for an image pickup electronic endoscope in which there is a solid-state image sensor disposed within a stiff distal end of the endoscope.

2. Description of the Prior Art

As is well recognized, a solid-state video camera may be formed by charge coupled devices (CDD) which are arranged in the form of a dual in-line IC package. The package has an imaging plane or input surface defined in a part of the top surface thereof, and is internally assembled with peripheral circuits. Accordingly, the overall size of the video camera will be as large as several times the dimension of the imaging plane. When it is desired to construct an endoscope utilizing such a solid-state video camera for taking a picture, a difficulty is experienced in the arrangement of the camera. Specifically, FIG. 2A shows the distal end 1 of an endoscope in which an objective lens assembly 2 is disposed. If a solid-state video camera 3 is disposed rearwardly of the lens assembly 2 in an orientation so that it is perpendicular to the length or the axial direction of the endoscope, the size of the solid-state video camera 3 requires that the diameter of the distal end 1 of the endoscope be increased, as illustrated in FIG. 2B, which is undesirable. Accordingly, to overcome such difficulty, an arrangement is disclosed in Japanese Laid-Open Patent Application No. 46,922/1983 in which a reflecting member 4 such as a prism as shown in FIG. 3A is disposed rearwardly of the objective lens assembly 2 within the distal end 1 of the endoscope so that the optical axis extending from the lens assembly 2 may be bent in a direction perpendicular to the length or the axial direction of the endoscope, thus permitting light for observation to impinge upon a solid-state video camera 3' which is now disposed so as to extend parallel to the axis of the endoscope. However, it will be appreciated from FIG. 3B that in this instance, because the solid-state video camera 3' is offset from the optical axis of the lens assembly 2, the camera 3' cannot be disposed in proximity to the center axis of the distal end 1, and hence stiff distal end 1 must still be of relatively large diameter so that the patient will be subjected to discomfort.

SUMMARY OF THE INVENTION

It is an object of the invention to provide an optical system for an endoscope utilizing a solid-state video camera which permits a picture to be taken wherein the length and diameter of the relatively stiff distal end of the endoscope which internally houses an objective lens assembly and the video camera can be minimized.

It is a further object of the invention to provide a variety of deflection prisms which permit a solid-state video camera to be disposed along or in proximity to the center axis of the distal end of an endoscope so that the maximum dimension of the video camera can be received within the extent of the greatest width of the distal end.

It is another object of the invention to provide a deflection prism which is applicable, not only to the optical system for an endoscope of direct view type, but also for endoscopes of lateral and oblique view types.

It is a still further object of the invention to provide an optical system including a prism, disposed in an optical path and which is formed of a material exhibiting a birefringence or which has a λ/2 phase film evaporated on one surface thereof so as to to be effective in preventing the occurrence of moiré fringes which tend to form in an image produced by a solid-state video camera.

It is an additional object of the invention to provide an optical system including a prism disposed in an optical path and which is formed of an infrared absorbing glass or which has an infrared reflecting coating applied to one surface thereof in order to remove unnecessary infrared rays.

BRIEF DESCRIPTION OF THE DRAWINGS

FIG. 18 is a schematic side elevation of an endoscope distal end having an optical system, prism and image sensor arranged in accordance with a fifth embodiment of this invention;

FIG. 19 is a diagram illustrating the configuration of a phase film which is used to prevent the occurrence of moiré fringes.

DETAILED DESCRIPTION OF PREFERRED EMBODIMENTS

Figure 1A:
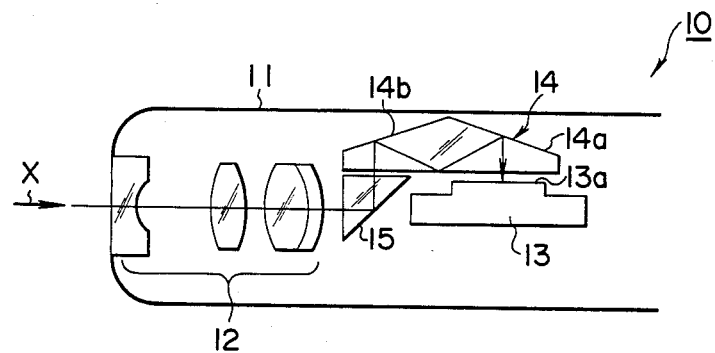
FIGS. 1A and 1B are a schematic side elevation and a schematic front view of an endoscope according to a first embodiment of the invention.
Figure 1B:
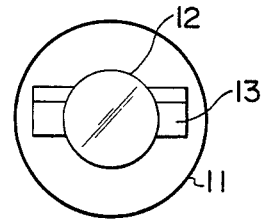
Figure 2A:
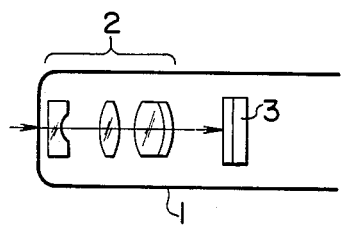
FIGS. 2A, 2B and FIGS. 3A and 3B illustrate conventional endoscopes, FIGS. 2A and 3A being schematic side elevations and FIGS. 2B and 3B being front views.
Figure 2B:
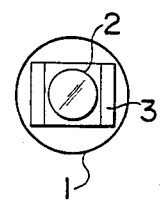
Figure 3A:
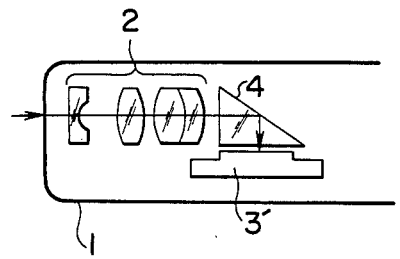
Figure 3B:
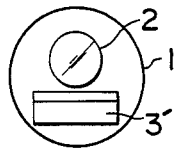

Referring to the drawings, several embodiments of the invention will now be described. Referring to FIGS. 1A and 1B initially, there is shown an optical system 10 for an endoscope of direct view type which is constructed according to the invention. As shown, the endoscope includes a distal end 11 having an objective lens assembly 12 disposed therein. It will be apparent from FIG. 1B that the lens assembly is disposed in substantially coaxial relationship with the center axis of the distal end 11. A solid-state video camera 13 is disposed along or near the center axis of the distal end 11 so that it is located in a region having the greatest width in the cross section of the distal end 11. An angled prism 14 includes a first reflecting surface 14a disposed opposite to an input surface 13a of the video camera 13 at an angle thereto, and a second reflecting surface 14b. Both the first and the second reflecting surfaces 14a and 14b comprises specular surfaces that may be implemented by aluminum coatings. A reflecting prism 15 is disposed rearward of the objective lens assembly 12. Light for observation which is incident on the distal end 11 in a direction indicated by an arrow X passes through the objective lens assembly 12 and is then reflected upward, as viewed in FIG. 1A, by the prism 15 to impinge upon the angled prism 14, the second reflecting surface 14b of which reflects the incident light, which is then subject to a total reflection at the bottom surface thereof to be reflected then by the first reflecting surface 14a, whereby it is emitted from the angled prism 14 to be focussed upon the input surface 13a of the video camera 13.

The described arrangement allows the solid-state video camera 13 to be disposed along or near the center axis of the distal end of the endoscope, whereby the camera 13 is situated within the distal end 11 so that the maximum dimension of the camera 13 is disposed in the region of the maximum width of the distal end. Since the angled prism 14 is received in a space which is left on one side of the input surface 13a of the solid-state video camera 13, it does not require any increase in the diameter of the distal end 11. In this manner, the diameter of the distal end 11 of the endoscope can be maintained at minimum.

Figure 4:
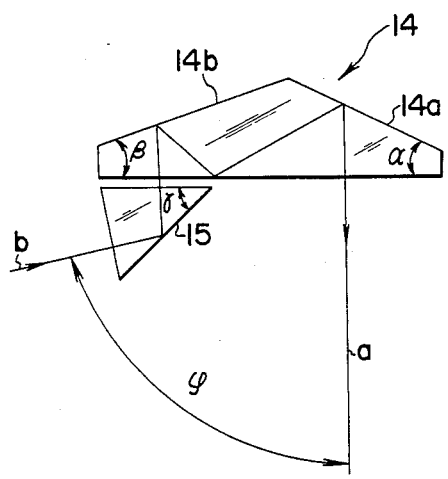
FIG. 4 is a detailed view of a prism used in the embodiment of FIG. 1.

FIG. 4 is a detailed view of the angled prism 14 and the reflecting prism 15 shown in FIG. 1A. In this Figure, a ray of light from the objective lens assembly 12 is denoted by b and a ray of light which is emitted from the angled prism 14 toward the video camera 13 by a. By representing the angles of inclination of the first reflecting surface 14a, the second reflecting surface 14b of the angled prism 14 and the reflecting surface of the reflecting prism 15 by $\alpha$, $\beta$ and $\gamma$, we have $$\alpha - \beta + \gamma = 90° - \phi/2,$$

where $\phi$ is the angle between the incoming and outgoing path segments b and a, respectively, for light impinging upon the input of prism means 15, 14.

The angled prism 14 and the reflecting prism 15 may be cemented together or may be spaced from each other with a narrow air gap therebetween. In addition, the angled prism 14 may serve as a cover glass for the input surface 13a of the video camera 13.

Figure 5:
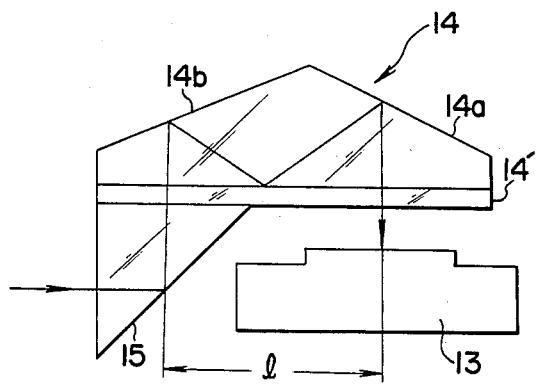
FIGS. 5 to 12 are schematic views, illustrating different prisms and optical systems which represent modifications of the embodiment shown in FIG. 1.

FIGS. 5 to 12 show several modifications of the embodiment shown in FIG. 1A. In FIG. 5, the bottom of the angled prism 14 shown in FIG. 1A is formed by a separate prism 14' in the form of a plate which is formed of a material exhibiting a reduced refractive index so that the light reflected by the second reflecting surface 14b of the prism 14 is subject to a total reflection at the boundary surface between the prisms 14, 14'. This arrangement functions in the similar manner as the embodiment of FIG. 1A while assuring the total reflection at the bottom surface of the angled prism 14 if the angled prism 14 and the reflecting prism 15 are cemented together.

Figure 6:
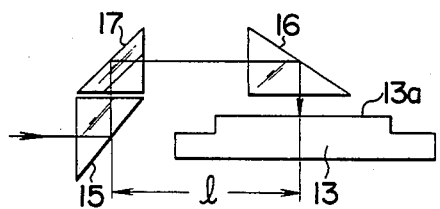

In FIG. 6, the angled prism 14 shown in the embodiment of FIG. 1A is replaced by a combination of a prism 16 which is angularly disposed in opposing relationship with the input surface 13a of the solid-state video camera 13, and a dach prism 17 which is positioned so as to cause light from the reflecting prism 15 to impinge upon the prism 16. In this instance, the both prisms 15 and 16 may also be constructed as dach prisms. In either instance, a arrangement operates in the similar manner as the embodiment of FIG. 1A. In the arrangement of FIG. 6, the prism 17 may not be a dach prism. It may be formed by a prism of triangular form which is easily polished, thus reducing the cost. By changing the distance l between the reflecting surfaces of the prisms 16 and 17, it may be used with a video camera 13 of any size.

Figure 7:
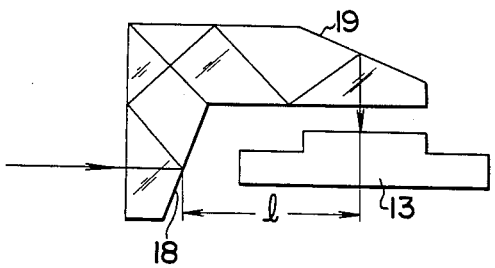

In FIG. 7, the combination of the angled prism 14 and the reflecting prism 15 shown in FIG. 1A is replaced by a pair of prisms 18 and 19 which are disposed as shown. This arrangement permits the distance l between the incident ray of light upon the video camera 13 and the first reflecting surface of the prism 18 to be increased as compared with the arrangment of FIG. 5, thus allowing the arrangement to be used with a solid-state video camera of a greater size than that shown in FIG. 5.

Figure 8:
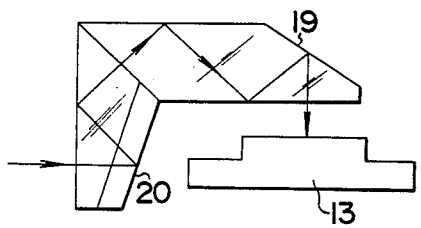

In FIG. 8, the prism 18 shown in FIG. 7 is replaced by a dach prism 20. In both instances, the arrangement operates in a similar manner as the embodiment of FIG. 1A while allowing a solid-state video camera 13 having an increased length to be used. It will be appreciated that the arrangement of FIG. 7 involves an odd number of reflections to produce an inverted image while the arrangement of FIG. 8 produces an erect image.

Figure 9:
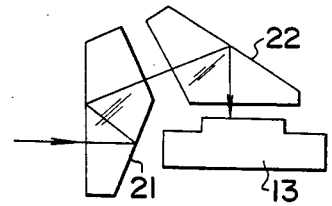

FIG. 9 shows an arrangement including a pair of prisms 21 and 22 and which permit the number of reflections to be reduced compared to the arrangement of FIG. 7. Either one of the prisms 21 or 22 may comprise a dach prism, thereby producing an erect image.

Figure 10:
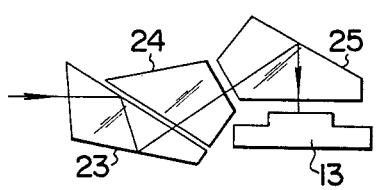

FIG. 10 illustrates an arrangement which makes use of three prisms 23, 24 and 25. The prism 25 may comprise a dach prism. When either prism 23 or 24 comprises a dach prism, an erect image is produced.

Figure 11:
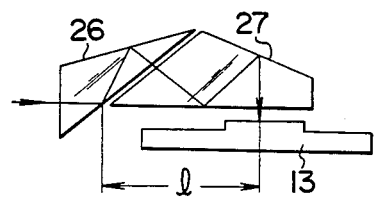

FIG. 11 illustrates an arrangement which uses a pair of prisms 26 and 27. It will be appreciated that this arrangement can be used with a solid-state video camera 13 of an increased size since the distance l can be increased as compared with the arrangement of FIG. 5. It is to be understood that any of the arrangements shown in FIGS. 9 to 11 operates in a similar manner as the embodiment of FIG. 1A.

Figure 12:
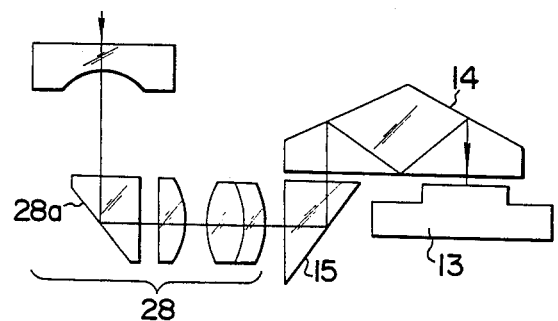

FIG. 12 illustrates an arrangement in which the objective lens assembly 12 of direct view type which is used in the embodiment of FIG. 1A is replaced by an objective lens assembly 28 of lateral view type including an intermediate prism 28a. If either prism 28a or 15 comprises a dach prism, an erect image is produced.

Figure 13:
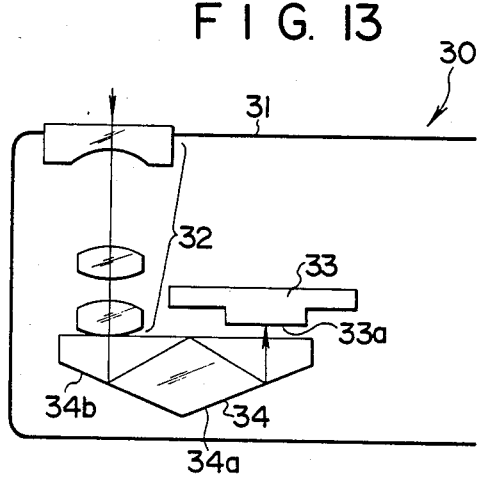
FIG. 13 is a schematic view of an optical system according to a second embodiment of the invention.

FIG. 13 shows an optical system for endoscope according to a second embodiment of the invention. Specifically, an endoscope 30 is of the lateral view type and has a distal end 31 in which an objective lens assembly 32 is disposed in a direction which is oriented substantially perpendicular to the center axis of the distal end 31. A solid-state video camera 33 is disposed along or near the center axis of the distal end 31. An angled prism 34 has a first reflecting surface 34a which is disposed at an angle with respect to and in opposing relationship with an input surface 33a of the video camera 33 and a second reflecting surface 34b. A ray of light which passes through the objective lens assembly 32 impinges upon the angled prism 34, and is sequentially reflected by the second and the first reflecting surfaces 34b and 34a, and is then emitted therefrom to be focussed upon the input surface 33a of the video camera 33. An erect image is produced if either the first or the second reflecting surface 34a or 34b of the prism 34 comprises a dach surface.

Figure 14:
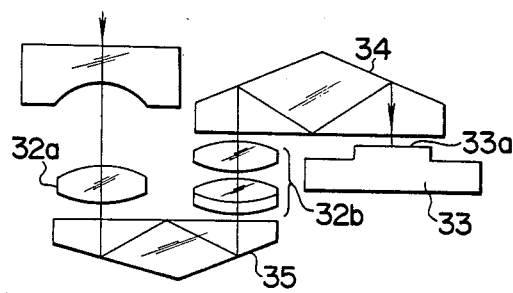
FIG. 14 is a schematic view of an optical system which is a modification of the embodiment shown in FIG. 13.

FIG. 14 shows a modification of the embodiment shown in FIG. 13 where the objective lens assembly 32 is divided into a first section 32a disposed on the front side of a second angled prism 35 and a second section 32b disposed on the rear portion of the prism 35 in order to accommodate for a relatively long overall length of the objective lens assembly 32. Either embodiment shown in FIGS. 13 and 14 permits the solid-state video camera 33 to be disposed in proximity to the center axis of the distal end 31a of the endoscope since the optical axis of the objective lens assembly is once directed laterally to one side of the input surface with respect to the center axis of the endoscope and then introduced to the reflecting surface which is angularly disposed in opposing relationship with the input surface 33a.

Figure 15:
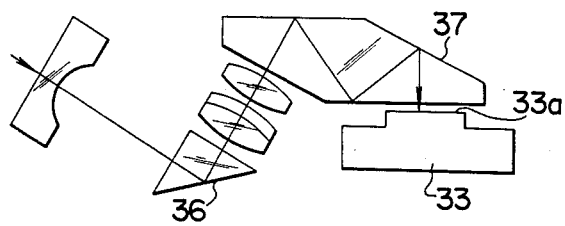
FIG. 15 is a schematic view of an optical system according to a third embodiment of the invention.
Figure 16:
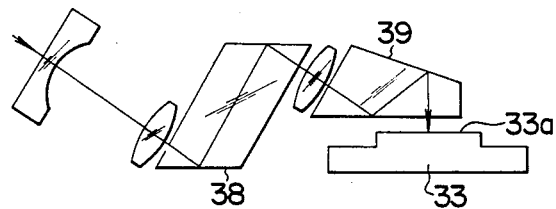
FIG. 16 is a schematic view of an optical system which represents a modification of the embodiment shown in FIG. 15.

FIG. 15 shows an optical system for endoscope according to a third embodiment of the invention. In this embodiment, the objective lens assembly is of an oblique view type and includes a prism 36 therein, and the optical system also includes a prism 37 which is disposed over the input surface 33a. FIG. 16 shows a modification of the arrangement shown in FIG. 15, including prisms 38 and 39. Either arrangement shown in FIGS. 15 and 16 can be applied with an endoscope of oblique view type while allowing the solid-state video camera 33 to be disposed in proximity to the center shaft of the distal end thereof. The arrangements shown in FIGS. 14, 15 and 16 are constructed with prisms which do not contain dach surfaces, thus reducing the cost while allowing an erect image to be produced.

Figure 17:
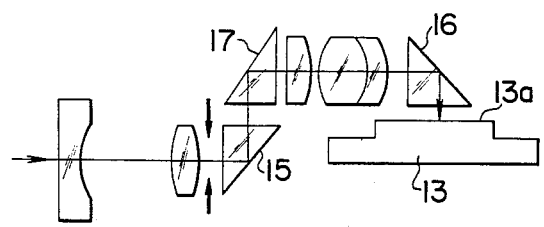
FIG. 17 is a schematic of an optical system and a prism used therein according to a fourth embodiment of the invention.

FIG. 17 shows a further modification of the modification shown in FIG. 16 where certain elements of the objective lens assembly may be disposed between prisms 16 and 17 in order to accommodate for an increased overall length of the objective lens assembly.

In FIG. 18, a solid-state video camera 40 is disposed within the distal end of an endoscope along the center axis thereof with a slight inclination, permitting ray of light from the associated objective lens assembly to impinge upon the input surface of the camera 40 while utilizing a single prism 41. The use of the single prism 41 reduces the cost required and produces a positive image. The prism may be formed of a colored glass and may serve as a color temperature conversion filter.

In each embodiment described above, if an input surface of the solid-state video camera is located at an increased distance from the objective lens assembly to prevent light from the lens assembly from being focussed upon the input surface, a relay lens or lenses may be interposed between the lens assembly and the input surface so as to permit the image to be focussed upon the input surface.

It should be noted that moiré fringes tend to be formed in an image which is produced by a solid-state video camera. The occurrence of such moiré fringes can be prevented by forming at least one of the prisms inserted in the optical path of a material such as quartz which exhibits birefringence. The occurrence of moiré fringes can also be prevented by evaporating phase films having a phase difference which is substantially equal to an odd multiple of one-half the wavelength in the form of fine dots arranged randomly, as indicated in FIG. 19, on at least one surface of the prism so that these dots totals to one-half the area of the surface.

Also, undesired infrared rays can be removed by forming at least one of the prisms inserted into the optical path by an infrared absorbing glass or by applying an infrared reflecting coating on at least one surface of such prism.

In the above description, a prism or prisms have been used to cause a reflection of a ray of light from the objective lens assembly. However, it should be understood that such prism or prisms may be replaced by mirrors.

What is claimed is:

1. An optical system adapted to be disposed within a housing that is located at a distal end of an endoscope and has a central axis situated longitudinally of such endoscope, said optical system including:
    an objective lens assembly for receiving light from an external object, a longitudinally extending image sensor disposed at said central axis, and prism means disposed for guiding light from said objective lens assembly downstream along an optical path toward a plane of incidence at a pickup surface of said image sensor;
    with said central axis positioned horizontally and said pickup surface being horizontal and facing upward, said pickup surface facing a bottom surface of said prism means through which light exits from said prism means;
    said prism means including at least two reflection surfaces:
    a first of said reflection surfaces directing a light beam received from the objective lens assembly along said optical path to a second of said reflection surfaces that reflects said light in a straight line through an exit surface of said prism means to impinge upon said pickup surface;
    said optical path deviating substantially from the longitudinal axis of the endoscope.

2. An optical system according to claim 1 in which the prism means also includes a third reflection surface disposed above and in front of the pickup surface; said third surface extending in the longitudinal direction of the endoscope and intersecting said path for reflecting light from the objective lens assembly in a direction away from the plane and through the second reflection surface.

3. An optical system according to claim 2 in which the prism means further includes a fourth reflection surface disposed along said path at a location between the first and third reflection surfaces to reflect said light and direct same to impinge upon the third reflection surface.

4. An optical system according to claim 3 in which the second, third and fourth reflection surfaces are formed in a single prism, and the third reflection surface constitutes an exit through which said light passes to leave the single prism.

5. An optical system according to claim 3 in which the prism means further includes a fifth reflection surface disposed along said path at a location between the first and the fourth reflection surfaces.

6. An optical system according to claim 5 in which the first and fifth reflection surfaces are formed in a first prism and the second, third and fourth reflection surfaces are formed in a second prism; said fifth reflection surface also constituting an incidence surface through which the light passes to enter the first prism, and the fourth reflection surface also constitutes an exit through which said light passes to leave the second prism.

7. An optical system according to claim 6 in which the prism means is provided with means for removing unnecessary infrared rays.

8. An optical system according to claim 6 in which the prism means is constructed of a material which exhibits birefringence.

9. An optical system according to claim 1 in which the prism means is provided with means for removing unnecessary infrared rays.

10. An optical system according to claim 1 in which the prism means is constructed of a material which exhibits birefringence.

11. An optical system according to claim 1 in which the pickup surface is positioned at least as high as said central axis.

12. An optical system adapted to be disposed within a housing that is located at a distal end of an endoscope and has a central axis situated longitudinally of the endoscope, said optical system including:

an objective lens assembly for receiving light from an external object, an axially extending image sensor, and prism means disposed for guiding light from said objective lens assembly downstream toward a plane of incidence at a pickup surface of said image sensor;

with said central axis positioned horizontally and said pickup surface facing upward, a first reflection surface of said prism means directing light incident upon the objective lens assembly downwardly from an input surface of said prism means, a second reflection surface of said prism means directing light reflected by the first reflecting surface upwardly, and a third reflection surface of said prism means directing light reflected by the second reflection surface to impinge on the pickup surface;

said first and second reflecting surfaces being formed in a single prism and the first reflecting surface constituting an output surface through which light exits the single prism and is directed downstream thereof.

* * * * *